(12) United States Patent
Sartor et al.

(10) Patent No.: US 12,121,286 B2
(45) Date of Patent: Oct. 22, 2024

(54) DEVICES AND METHODS FOR SHALLOW DEPTH ABLATION

(71) Applicant: Covidien LP, Mansfield, MA (US)

(72) Inventors: Joe D. Sartor, Longmont, CO (US); Nikolai D. Begg, Wellesley, MA (US)

(73) Assignee: Covidien LP, Mansfield, MA (US)

( * ) Notice: Subject to any disclaimer, the term of this patent is extended or adjusted under 35 U.S.C. 154(b) by 638 days.

(21) Appl. No.: 17/324,801

(22) Filed: May 19, 2021

(65) Prior Publication Data
US 2022/0022941 A1 Jan. 27, 2022

Related U.S. Application Data

(60) Provisional application No. 63/055,436, filed on Jul. 23, 2020, provisional application No. 63/055,421, filed on Jul. 23, 2020.

(51) Int. Cl.
| | | |
|---|---|---|
| *A61B 18/12* | (2006.01) | |
| *A61B 18/14* | (2006.01) | |
| *A61B 17/29* | (2006.01) | |
| *A61B 18/00* | (2006.01) | |

(52) U.S. Cl.
CPC .. *A61B 18/1445* (2013.01); *A61B 2017/2902* (2013.01); *A61B 2017/2926* (2013.01); *A61B 2018/00577* (2013.01); *A61B 2018/1467* (2013.01)

(58) Field of Classification Search
CPC . A61B 18/14; A61B 18/1445; A61B 18/1485; A61B 2018/126
See application file for complete search history.

(56) References Cited

U.S. PATENT DOCUMENTS

| | | | |
|---|---|---|---|
| 5,462,545 A | | 10/1995 | Wang et al. |
| 5,922,002 A | * | 7/1999 | Yoon ................... A61F 6/20 |
| | | | 606/205 |
| 6,039,736 A | | 3/2000 | Platt, Jr. |
| 6,071,283 A | | 6/2000 | Nardella et al. |
| 6,080,152 A | | 6/2000 | Nardella et al. |
| 6,152,924 A | * | 11/2000 | Parins ................ A61B 18/1445 |
| | | | 606/174 |
| 7,799,026 B2 | | 9/2010 | Schechter et al. |
| 8,574,229 B2 | | 11/2013 | Eder et al. |
| 8,679,114 B2 | | 3/2014 | Chapman et al. |
| 8,784,410 B2 | | 7/2014 | Dunning |

(Continued)

*Primary Examiner* — Daniel W Fowler
(74) *Attorney, Agent, or Firm* — Carter, DeLuca & Farrell LLP

(57) ABSTRACT

An end effector assembly of a surgical device for shallow depth ablation includes first and second jaw members movable between open and closed positions and including hemicylindrical surfaces that cooperate to define a cylindrical cavity in the closed position for capturing tissue therebetween. At least one electrode array includes a plurality of first and second electrode portions disposed on or within at least one of the hemicylindrical surfaces and extending annularly at least partially thereabout. The plurality of first and second electrode portions are configured to be energized with electrosurgical energy at different potentials to thereby conduct electrosurgical energy between adjacent first and second electrode portions and through captured tissue to affect shallow depth ablation of captured tissue in the closed position of the first and second jaw members.

15 Claims, 13 Drawing Sheets

(56) References Cited

U.S. PATENT DOCUMENTS

| | | |
|---|---|---|
| 9,119,650 B2 | 9/2015 | Brannan et al. |
| 9,247,992 B2 | 2/2016 | Ladtkow et al. |
| 9,750,568 B2 | 9/2017 | Sobotka |
| 9,757,181 B2 | 9/2017 | Podhajsky et al. |
| 9,918,794 B2 | 3/2018 | Wallace et al. |
| 2008/0172052 A1* | 7/2008 | Eder .................. A61B 18/1442 606/50 |
| 2012/0116382 A1 | 5/2012 | Ku et al. |
| 2012/0116416 A1 | 5/2012 | Neff et al. |
| 2012/0136350 A1 | 5/2012 | Goshgarian et al. |
| 2013/0085496 A1* | 4/2013 | Unger ................ A61B 18/1442 606/45 |
| 2013/0317495 A1 | 11/2013 | Brannan |
| 2014/0250661 A1 | 9/2014 | Vreeman et al. |
| 2014/0378965 A1 | 12/2014 | Atwell |
| 2016/0235473 A1* | 8/2016 | Hagland ............ A61B 18/1442 |

\* cited by examiner

DEVICES AND METHODS FOR SHALLOW DEPTH ABLATION

CROSS-REFERENCE TO RELATED APPLICATIONS

This application claims the benefit of, and priority to, U.S. Provisional Patent Application Nos. 63/055,421 and 63/055,436, both titled "DEVICES AND METHODS FOR SHALLOW DEPTH ABLATION" and filed on Jul. 23, 2020. The entire contents of each of these applications is hereby incorporated herein by reference.

FIELD

The present disclosure relates generally to energy-based tissue treatment and, more specifically, to devices and methods for shallow depth ablation of tissue such as, for example, for denervation of sympathetic ovarian nerves.

BACKGROUND

Ovarian sympathetic neural activity can cause or exacerbate several ovarian conditions, including common endocrine disorders affecting women of reproductive ages such as Polycystic Ovary Syndrome (PCOS) and Premenstrual Dysphoric Disorder (PMDD). Scientific literature suggests that ovarian hormonal secretion is regulated by sympathetic nervous activity to the ovary. The sympathetic nervous system (SNS) is a primarily involuntary bodily control system typically associated with stress responses. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. Signals sent via these and other fibers can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the ovarian SNS has been identified experimentally and in humans as a likely contributor to the complex pathophysiology of PCOS.

SUMMARY

As used herein, the term "distal" refers to the portion that is described which is farther from an operator (whether a surgeon or surgical robot), while the term "proximal" refers to the portion that is being described which is closer to the user. Terms including "generally," "about," "substantially," and the like, as utilized herein, are meant to encompass variations up to and including plus or minus 10 percent. Further, any or all of the aspects described herein, to the extent consistent, may be used in conjunction with any or all of the other aspects described herein.

Provided in accordance with aspects of the present disclosure is a surgical device for shallow depth ablation including an end effector assembly having first and second jaw members, at least one of which is movable relative to the other between an open position and a closed position. Each of the first and second jaw members includes an inner surface, an outer surface, and a hemicylindrical surface recessed relative to the inner surface to define a hemicylindrical cavity. In the closed position of the first and second jaw members, the hemicylindrical surfaces cooperate to define a cylindrical cavity extending transversely across the first and second jaw members and open at either end of the cylindrical cavity. In the closed position of the first and second jaw members, the first and second jaw members are configured to capture tissue within the cylindrical cavity. At least one electrode array includes a plurality of first electrode portions and a plurality of second electrode portions disposed on or within at least one of the hemicylindrical surfaces and extending annularly at least partially about the at least one hemicylindrical surface. The plurality of first and second electrode portions are configured to be energized with electrosurgical energy at different potentials to thereby conduct electrosurgical energy between adjacent electrode portions of different potential and through captured tissue to affect shallow depth ablation of captured tissue in the closed position of the first and second jaw members.

In an aspect of the present disclosure, the plurality of first electrode portions and the plurality of second electrode portions are arranged in alternating, spaced-apart relation annularly about at least a portion of the at least one hemicylindrical surface.

In another aspect of the present disclosure, each electrode portion of the plurality of first electrode portions is a first electrode leg extending in substantially parallel orientation relative to a longitudinal axis of the hemicylindrical cavity defined by the at least one hemicylindrical surface and each electrode portion of the plurality of second electrode portions is a second electrode leg extending in substantially parallel orientation relative to a longitudinal axis of the hemicylindrical cavity defined by the at least one hemicylindrical surface.

In another aspect of the present disclosure, the plurality of first and second electrode portions extend annularly at least 90 degrees about the at least one hemicylindrical surface; in aspects, at least 180 degrees.

In still another aspect of the present disclosure, the at least one electrode array includes a flex circuit. Additionally or alternatively, the at least one electrode array includes a flexible, insulative substrate and the first and second electrode portions are printed onto the substrate as conductive traces.

In yet another aspect of the present disclosure, the first and second jaw members are substantially linear. Additionally or alternatively, the first and second jaw members are curved along at least a portion of the lengths thereof.

In still yet another aspect of the present disclosure, at least one of the first or second jaw members is at least partially compressible to reduce an amount of pressure applied to tissue captured within the cylindrical cavity.

Provided in accordance with aspects of the present disclosure is another surgical device for shallow depth ablation. The surgical device includes a shaft, a foot coupled to a distal end portion of the shaft and defining a distal face having first and second side portions and first and second end portions. An electrode array is disposed on the foot and includes at least one first electrode and at least one second electrode. The at least one first electrode includes a base extending along the first side portion of the distal face of the foot and a plurality of spaced-apart legs extending from the base at least partially across the distal face. The at least one second electrode includes a base extending along the second side portion of the distal face of the foot and a plurality of spaced-apart legs extending from the base at least partially across the distal face to at least partially overlap the legs of the at least one first electrode. The legs of the at least one first and second electrodes are arranged in alternating, spaced-apart relation in a direction extending between the first and second end portions of the distal face. The at least one first and second electrodes are configured to be energized with electrosurgical energy at different potentials to thereby conduct electrosurgical energy between the legs of the at least one first and second electrodes and through tissue in contact with the distal face to affect shallow depth ablation.

In an aspect of the present discourse, the at least one first electrode includes one first electrode disposed on a first area of the distal face and another first electrode disposed on a second area of the distal face. Likewise, the at least one second electrode may include one second electrode disposed on the first area of the distal face and another second electrode disposed on the second area of the distal face. The first area may be a toe portion of the distal face and/or the second area may be a heel portion of the distal face.

In another aspect of the present disclosure, the one first and second electrodes are independently activatable relative to the another first and second electrodes.

In still another aspect of the present disclosure, the surgical device further includes an actuation rod extending through the shaft. The foot is pivotably coupled to the distal end portion of the shaft and operably coupled to the actuation rod such that translation of the actuation rod pivots the foot relative to the shaft between a first position and a second position.

In yet another aspect of the present disclosure, the distal face includes a toe portion and a heel portion. In the first position of the foot, the toe portion of the distal face is presented for contacting tissue and, in the second position of the foot, both the toe portion and the heel portion of the distal face are presented for contacting tissue. The at least one first electrode includes one first electrode disposed on the toe portion and another first electrode disposed on the heel portion, and wherein the at least one second electrode includes one second electrode disposed on the toe portion and another second electrode disposed on the heel portion.

In still yet another aspect of the present disclosure, the electrode array includes a flex circuit and/or a flexible, insulative substrate having the at least one first and second electrodes printed thereon as conductive traces.

Also provided in accordance with aspects of the present disclosure is a method of shallow depth ablation including positioning a hemicylindrical surface having an electrode array disposed thereon or therein in contact with tissue containing nerves. The electrode array includes a plurality of first electrode portions and a plurality of second electrode portions arranged in alternating, spaced-apart relation relative to one another and extending annularly about at least 90 degrees of the at least hemicylindrical surface. The method further includes activating the electrode array such that the plurality of first electrode portions is energized with electrosurgical energy at a potential and the plurality of second electrode portions is energized with electrosurgical energy at a different potential such that electrosurgical energy is conducted between adjacent first and second electrode portions and through tissue in contact with the hemicylindrical surface to affect shallow depth ablation.

In accordance with aspects of the present disclosure, another surgical device for shallow depth ablation is provided including a shaft defining a longitudinal axis and an end effector assembly disposed at a distal end of the shaft. The end effector assembly includes first and second jaw members. At least one of the first or second jaw members is movable relative to the other between a spaced-apart position and an approximated position. The first jaw member includes a first tissue-contacting surface including a hemicylindrical cavity defined therein. The second jaw member includes a second tissue contacting surface defining a substantially planar configuration. In the approximated position of the first and second jaw members, the second jaw member encloses the hemicylindrical cavity of the first jaw member. First and second electrode array portions are disposed on the first and second tissue-contacting surfaces, respectively, such that, in the approximated position of the first and second jaw members, the first and second electrode array portions extend about at least a portion of a perimeter of the enclosed hemicylindrical cavity. Each of the first and second electrode array portions includes first electrode legs and second electrode legs at least partially intertwined with one another and configured to be energized with electrosurgical energy at different potentials to thereby conduct electrosurgical energy between adjacent electrode legs of different potential and through tissue captured within the hemicylindrical cavity to affect shallow depth ablation of captured tissue in the approximated position of the first and second jaw members.

In an aspect of the present disclosure, the first and second electrode arrays are disposed on a single, continuous flex circuit. In such aspects, the first and second jaw members may be movably connected to one another via a living hinge. Additionally, the single, continuous flex circuit may extend across the living hinge from the first tissue-contacting surface to the second tissue-contacting surface.

In another aspect of the present disclosure, the first tissue-contacting surface is disposed in substantially perpendicular orientation relative to the longitudinal axis. In such aspects, the second jaw member may be movable relative to the first jaw member such that, in the approximated position of the first and second jaw members, the second tissue-contacting surface is disposed in substantially perpendicular orientation relative to the longitudinal axis.

In still another aspect of the present disclosure, in the approximated position, a portion of the first tissue-contacting surface is configured to contact a portion of the second tissue-contacting surface. In such aspects, the first and second electrode array portions are configured such that, even with the first and second tissue-contacting surfaces contacting one another, none of the first electrode legs and second electrode legs contact each other.

In yet another aspect of the present disclosure, the first electrode legs and the second electrode legs of each of the first and second electrode array portions are arranged in alternating, spaced-apart relation relative to one another.

In still yet another aspect of the present disclosure, the first and second electrode array portions each include a flexible, insulative substrate having the respective first and second electrode legs thereof printed onto the substrate as conductive traces.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
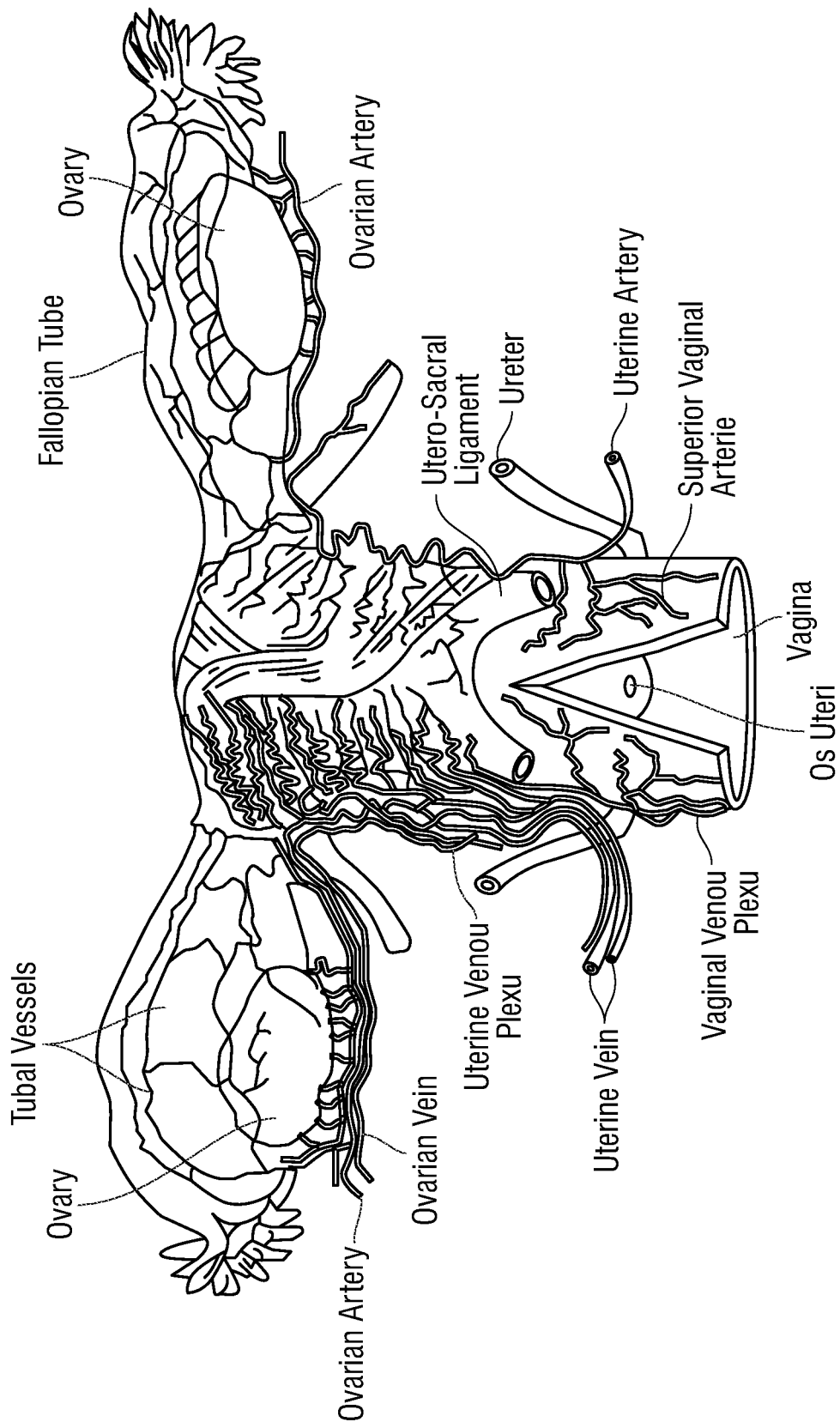
FIG. 1 is an anatomical view of a human female reproductive system and associated tissues.

Referring generally to FIG. 1, the human female reproductive system anatomy and associated tissues are illustrated. Shallow depth ablation (also referred to as surface ablation) in accordance with the devices and methods of the present disclosure may be performed, for example, during an ovarian denervation procedure. However, shallow depth ablation in accordance with the devices and methods of the present disclosure may also be utilized for denervation of other nerves and/or for different purposes.

With regard to ovarian denervation procedures, shallow depth ablation may be directed at or near one or more anatomical structures having a relatively high concentration of ovarian nerves. In some aspects, for example, the shallow depth ablation may be directed at or near a portion of the ovarian artery, a branch of the ovarian artery, an ostium of the ovarian artery, a portion of the ovarian vein, a branch of the ovarian vein, an ostium of the ovarian vein, and/or another suitable structure (e.g., another suitable structure extending along the suspensory ligament) in the vicinity of and/or containing ovarian nerves. In other aspects, the shallow depth ablation may be directed at or near a vessel or chamber wall (e.g., a wall of the ovarian artery, the ovarian vein, and/or another suitable structure). For example, with regard to the ovarian artery, the shallow depth ablation can be directed at the nerves in the ovarian plexus, which lay at least partially within and/or adjacent to the adventitia of the ovarian artery.

Shallow depth ablation, as utilized herein, refers to the application of energy to tissue, e.g., tissue including nerves therein, to heat the tissue (and nerves) for the purposes of thermal alteration of the tissue without or with minimal thermal-ablation of the tissue. For example, with respect to tissue denervation, shallow depth ablation may be performed to thermally alter the nerves to disrupting neural function by slowing or potentially blocking the conduction of neural signals, thereby producing a prolonged or permanent reduction in sympathetic activity. Shallow depth ablation, in such instances, induces thermal alteration of the tissue (and nerves) to achieve the denervation, but avoids or minimizes thermally-ablating the tissue (and nerves) by maintaining a target temperature of less than about 45 degrees C. In some configurations, the shallow depth ablation may treat tissue to a depth of from about 0.5 mm to about 3 mm from a surface of a tissue structure, although other depths are also contemplated.

Figure 2:
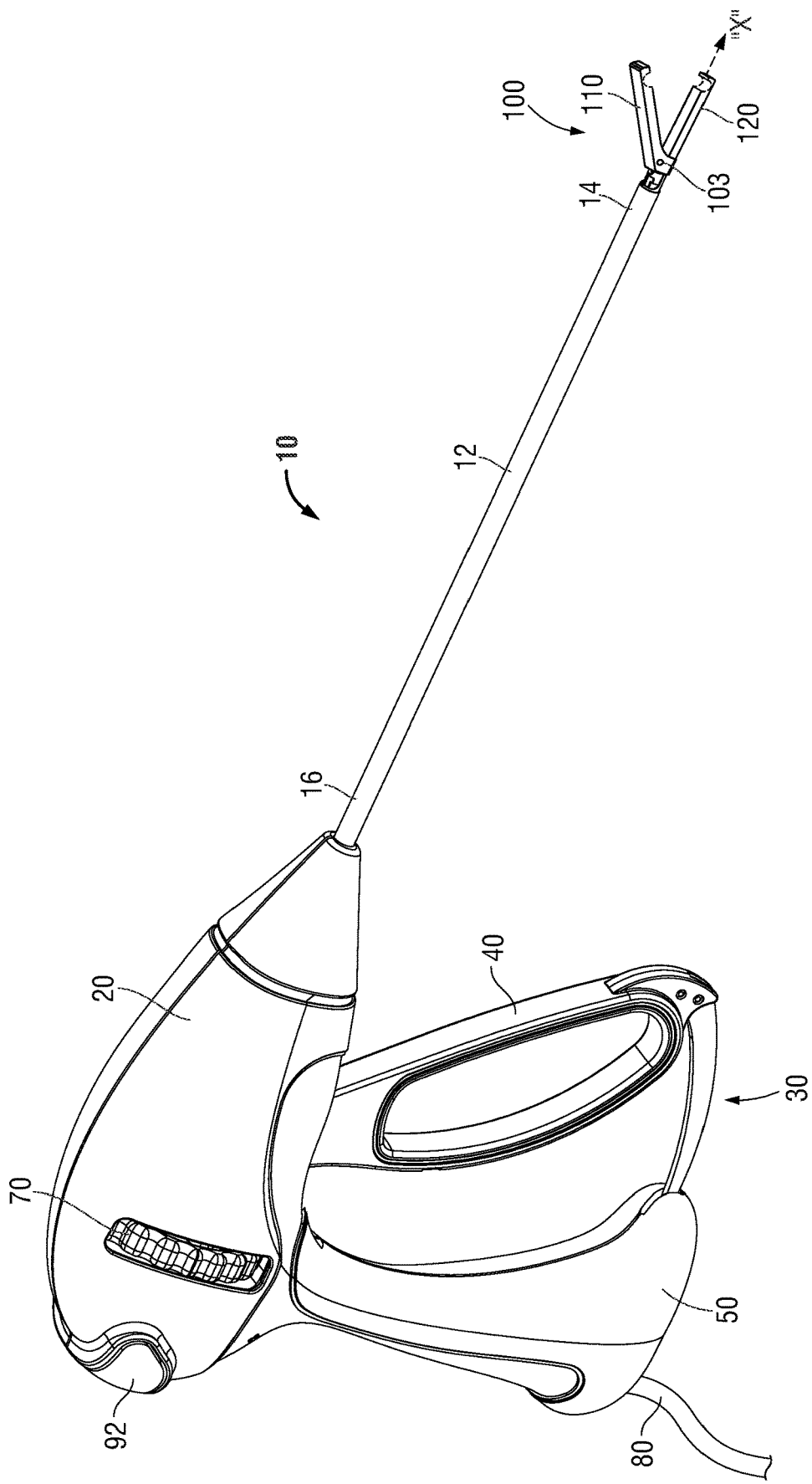
FIG. 2 is a front, perspective view of a surgical device configured for use in accordance with the present disclosure.

Turning to FIG. 2, a shaft-based surgical device 10 provided in accordance with the present disclosure includes a housing 20, a handle assembly 30, a rotating assembly 70, and an end effector assembly 100. Device 10 further includes a shaft 12 having a distal end 14 configured to mechanically engage end effector assembly 100 and a proximal end 16 that mechanically engages housing 20. Device 10 also includes a cable 80 that connects device 10 to an energy source (not shown), e.g., electrosurgical generator 90 (FIG. 3) or 1140 (FIG. 9), for supplying bipolar electrosurgical energy to end effector assembly 100 for treating tissue therewith, although device 10 may alternatively be configured as a battery powered device. An activation button 92 is disposed on housing 20 to enable the selective supply of energy from the energy source to end effector assembly 100 for treating tissue therewith.

With continued reference to FIG. 2, handle assembly 30 includes fixed handle 50 and a movable handle 40. Fixed handle 50 is integrally associated with housing 20 and handle 40 is movable relative to fixed handle 50. Rotating assembly 70 is rotatable in either direction to rotate end effector assembly 100 about a longitudinal axis of shaft 12. Housing 20 and/or shaft 12 houses the internal working components of device 10 such as, for example, a drive assembly (not shown) that operably interconnects movable handle 40 with end effector assembly 100, as detailed below.

End effector assembly 100 is shown attached at a distal end 14 of shaft 12 and includes a pair of opposing jaw members 110 and 120. End effector assembly 100 is designed as a unilateral assembly, i.e., where jaw member 120 is fixed relative to shaft 12 and jaw member 110 is movable about pivot 103 relative to shaft 12 and fixed jaw member 120. However, end effector assembly 100 may alternatively be configured as a bilateral assembly, i.e., where both jaw member 110 and jaw member 120 are movable about pivot 103 relative to one another and to shaft 12 or may be configured to enable movement of one or both of jaw members 110, 120 in any other suitable manner. Jaw members 110, 120 of end effector assembly 100 are described in greater detail below. Movable handle 40 of handle assembly 30 is ultimately connected to the drive assembly (not shown) that, together, mechanically cooperate to impart movement of jaw members 110 and 120 between an open position and a closed position. As shown in FIG. 2, movable handle 40 is initially spaced-apart from fixed handle 50 and, correspondingly, jaw members 110, 120 are in the open position. Movable handle 40 is actuatable from this initial position to a depressed position corresponding to the closed position of jaw members 110, 120 (see FIG. 5B).

Figure 3:
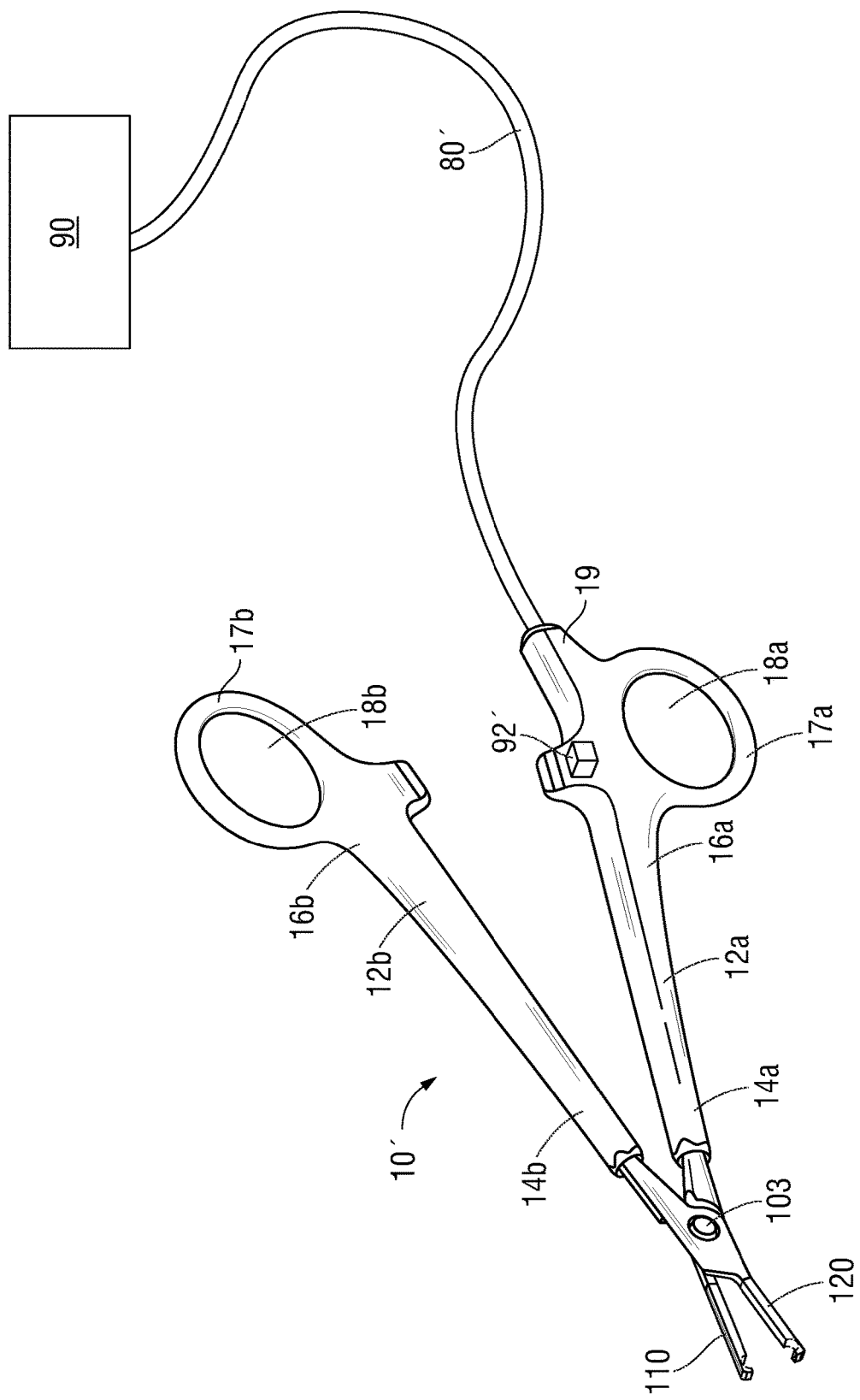
FIG. 3 is a front, perspective view of another surgical device configured for use in accordance with the present disclosure.

With reference to FIG. 3, a hemostat-style surgical device 10' provided in accordance with the present disclosure is shown including two shafts 12a and 12b, each having a proximal end 16a and 16b, and a distal end 14a and 14b, respectively. Similar to device 10 (FIG. 2), device 10' is configured for use with end effector assembly 100. More specifically, jaw members 110 and 120 of end effector assembly 100 are attached to distal ends 14a and 14b of shafts 12a and 12b, respectively. Distal ends 14a and 14b of shafts 12a and 12b, respectively, are pivotably connected about a pivot 103, thereby pivotably connecting, jaw members 110 and 120 of end effector assembly 100 about pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

One of the shafts, e.g., shaft 12b, includes a proximal shaft connector 19 that is designed to connect the device 10' to an electrosurgical generator 90 by way of a cable 80' to enable the supply of bipolar electrosurgical energy from electrosurgical generator 90 to end effector assembly 100. One of the shafts, e.g., shaft 12b, may further include an activation button 92' disposed thereon to enable the selective supply of bipolar electrosurgical energy from electrosurgical generator 90 to end effector assembly 100 for treating tissue therewith.

Figure 4:
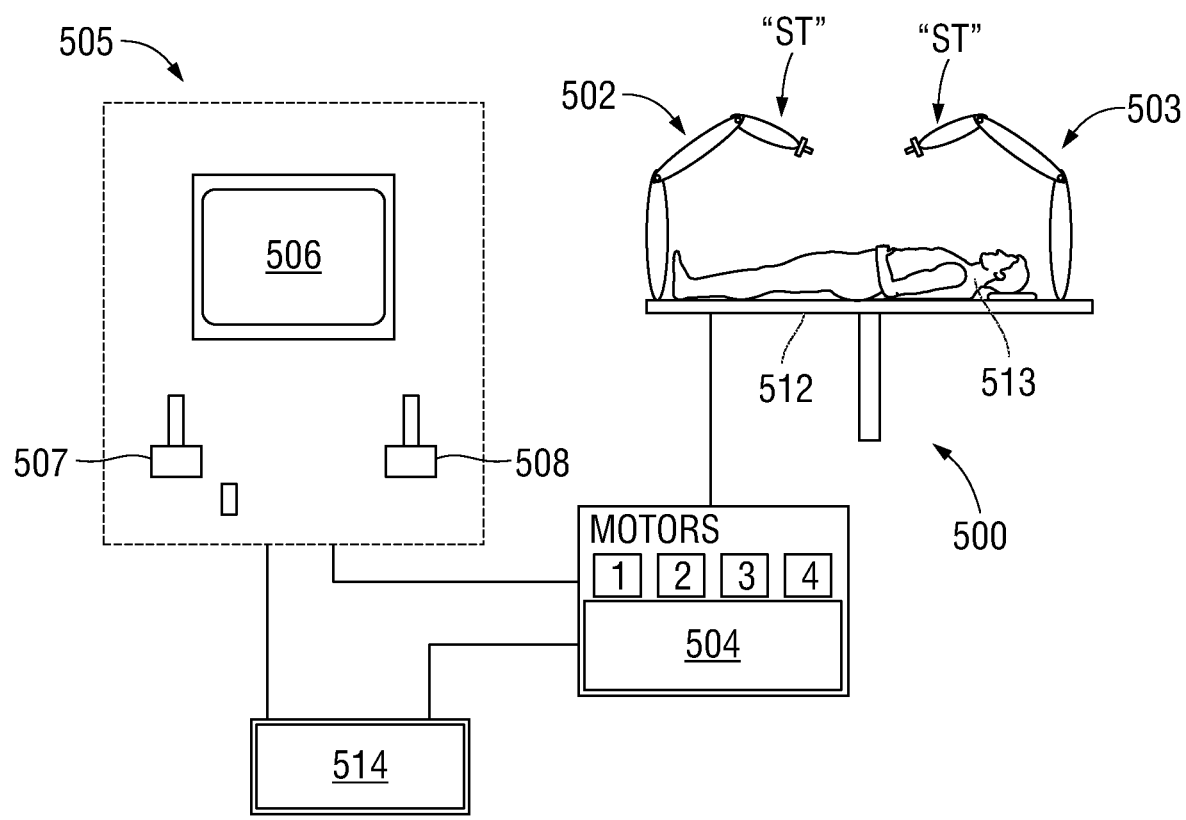
FIG. 4 is a schematic illustration of a robotic surgical system configured for use in accordance with the present disclosure.

Referring to FIG. 4, a robotic surgical system 500 configured for use in accordance with the present disclosure is provided. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, preoperative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be, for example, end effector assembly 100 (FIGS. 2 and 3), thus providing the functionality of devices 10, 10' (FIGS. 2 and 3, respectively) on a robotic platform.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

Figure 5A:
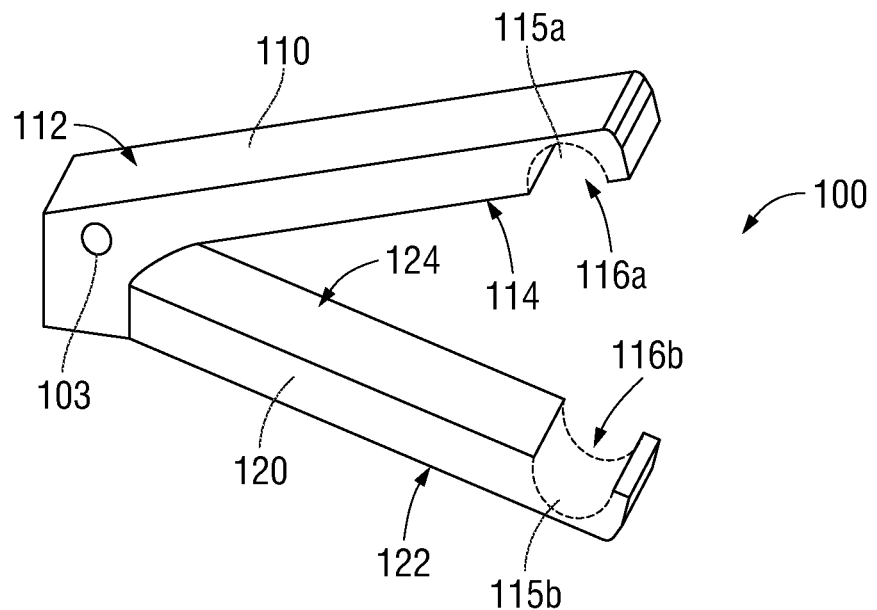
FIGS. 5A and 5B are enlarged, front, perspective views of an end effector assembly provided in accordance with the present disclosure disposed in open and closed positions, respectively, the end effector assembly configured for use with the surgical device of FIG. 2, the surgical device of FIG. 3, the robotic surgical system of FIG. 4, or any other suitable surgical device or system.
Figure 5B:
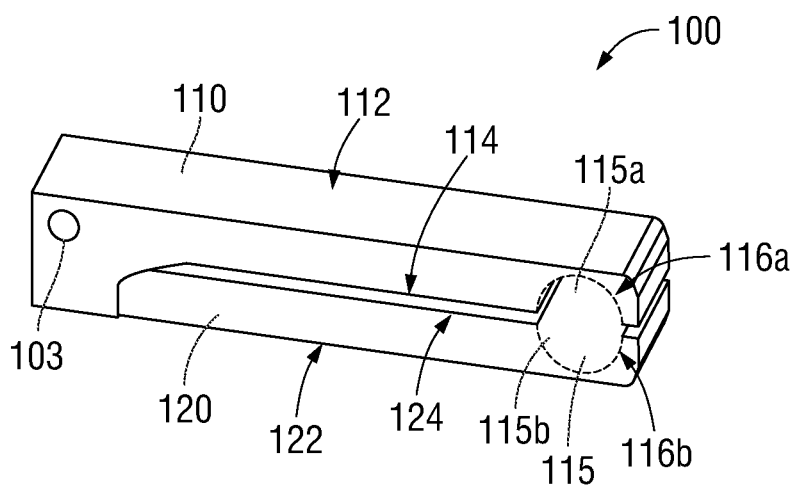

Turning to FIGS. 5A and 5B, end effector assembly 100, as noted above, is configured for use with device 10 (FIG. 2), device 10' (FIG. 3), system 500 (FIG. 4), or any other suitable surgical device or system, and includes first and second jaw members 110, 120.

Each jaw member 110, 120 includes an outer surface 112, 122 and an inner surface 114, 124, respectively. Inner surfaces 114, 124 are movable relative to one another between a spaced-apart position and an approximated position in response to movement of jaw members 110, 120 between the open and closed positions (see FIGS. 5A and 5B, respectively). Jaw members 110, 120 may be formed from rigid material, e.g., stainless steel, a rigid thermoplastic, a reinforced polymeric material, etc., such that jaw members 110, 120 resist flexion when closed about tissue, or may be formed at least partially from a compliant material (with or without a more-rigid structural frame or backing), e.g., PTFE, rubber, a compliant thermoplastic, etc., such that jaw members 110, 120 at least partially conform about tissue in the closed position.

Each jaw member 110, 120 further includes a cavity 115a, 115b defined within the respective inner surface 114, 124 thereof. Cavities 115a, 115b define substantially hemicylindrical configurations and extend transversely across jaw members 110, 120 such that, in the closed position of jaw members 110, 120, corresponding to the approximated position of inner surfaces 114, 124, cavities 115a, 115b cooperate to define a substantially cylindrical cavity 115 (see FIG. 5B) extending transversely through jaw members 110, 120 and open at either end thereof. Although cavity 115 (FIG. 5B) is shown having a cylindrical configuration, other substantially cylindrical configurations are also contemplated such as, for example, oval-shaped configurations, higher-order polygonal configurations that generally approximate a cylinder, e.g., an octagon, decagon, dodecagon, etc., and other suitable cylindrical-approximating configurations.

Figure 6:
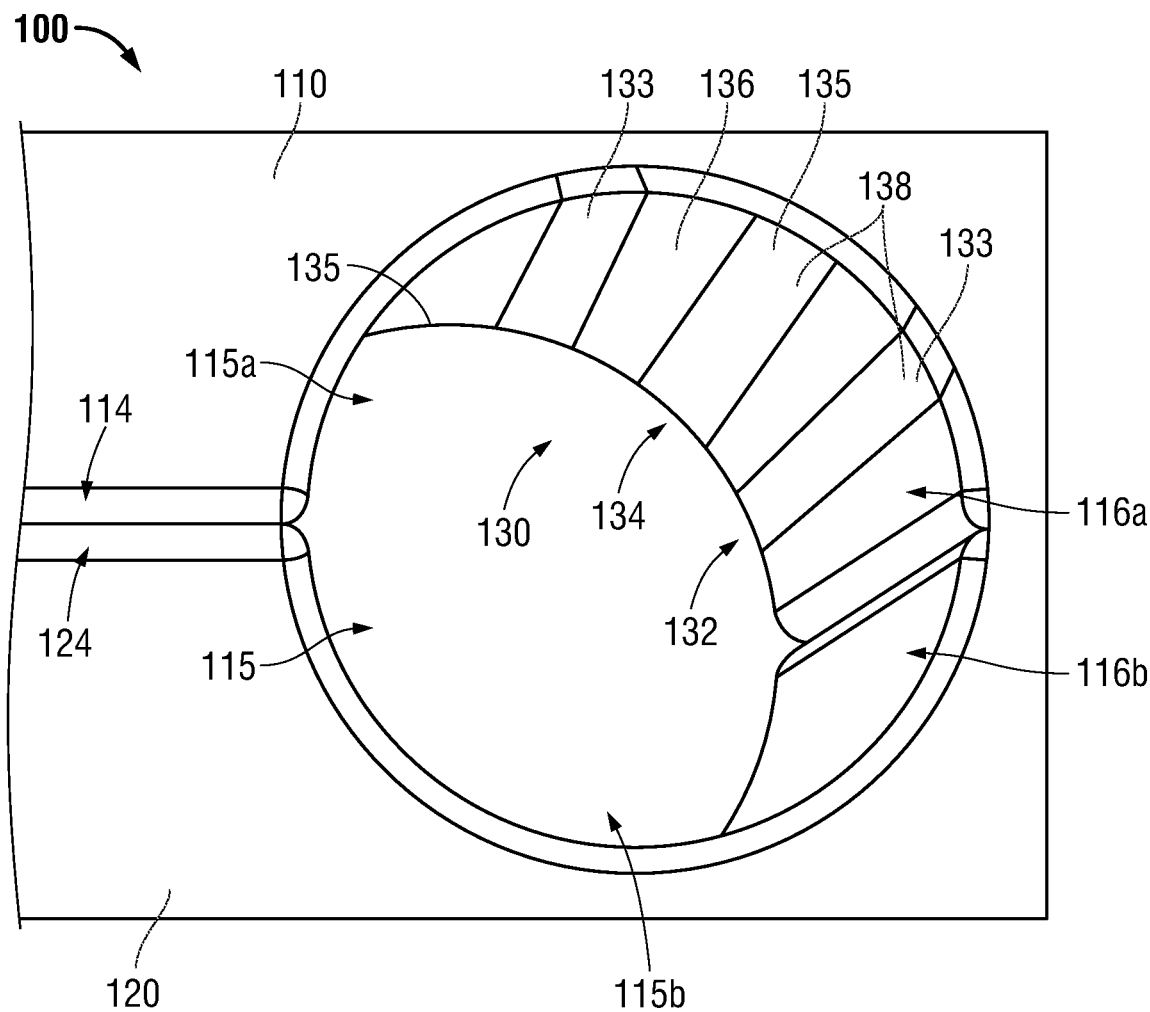
FIG. 6 is an enlarged, side, perspective view of the end effector assembly of FIGS. 5A and 5B disposed in the closed position.

With additional reference to FIG. 6, cavities 115a, 115b are defined by substantially hemicylindrical surfaces 116a, 116b, respectively, of jaw members 110, 120. One or both surfaces 116a, 116b, includes an electrode array 130. Each electrode array 130 may be disposed on and/or within the hemicylindrical surface 116a, 116b of the corresponding jaw member 110, 120. More specifically, each electrode array 130 may be a flex circuit that is affixed to the corresponding hemicylindrical surface 116a, 116b, or may otherwise be deposited, sprayed, sputtered, adhered, overmolded, mechanically secured, etc. on and/or within hemicylindrical surface 116a and/or hemicylindrical surface 116b.

Each electrode array 130 includes one or more first electrodes 132 and one or more second electrodes 134. First and second electrodes 132, 134 are electrically isolated from one another and configured to be energized to different potentials. Where plural first electrodes 132 are provided, two or more of the first electrodes 132 may be electrically connected to one another and/or connected to a common electrical connector such that the two or more first electrodes are commonly energizable, or may be independently connected to enable independent energization. Likewise, where plural second electrodes 134 are provided, two or more of the second electrodes 134 may be electrically connected to one another and/or connected to a common electrical connector such that the two or more second electrodes are commonly energizable, or may be independently connected to enable independent energization.

Each electrode 132, 134 includes a plurality of electrode legs 133, 135. Electrodes 132, 134 are arranged such that electrode legs 133, 135 are arranged in alternating, spaced-apart relation extending annularly about at least a portion of the corresponding hemicylindrical surface 116a, 116b while each leg 133, 135 extends substantially longitudinally relative to longitudinal axes defined by the corresponding hemicylindrical surface 116a, 116b (transverse to longitudinal axes of the jaw members 110, 120). In aspects, electrode legs 133, 135 define generally linear strips that extend transversely across the corresponding jaw member 110, 120 within the cavity 115a, 115b thereof, although other configurations such as curved, angled, combinations of differently configured legs 133, 135, etc. are also contemplated. The alternating electrode legs 133, 135 may be equally spaced or spaced according to any suitable spacing pattern including two or more different spacings.

Continuing with reference to FIGS. 5A-6, with respect to configurations where the at least one electrode array 130 is a flex circuit, the electrode array 130 may include a flexible, electrically-insulative substrate 136, e.g., BoPET (biaxially-oriented polyethylene terephthalate), including electrically-conductive circuit traces 138, e.g., copper, printed thereon to define electrodes 132, 134, and may be adhered or otherwise affixed atop the corresponding hemicylindrical surface 116a, 116b and/or other portions of jaw members 110, 120. Alternatively, jaw member 110 and/or jaw member 120 may be formed at least partially from an electrically-insulative material or may include an electrically-insulative cover, e.g., coating, overmold, etc., disposed on the hemicylindrical surface 116a, 116b, respectively, thereof, with electrodes 132, 134 disposed thereon or therein to main electrical isolation.

The electrodes 132, 134 of each electrode array 130 may extend: at least 90 degrees about the cavity 115a, 115b defined by the hemicylindrical surface 116a, 116b of the corresponding jaw member 110, 120; at least 120 degrees; at least 150 degrees; or substantially 180 degrees. Thus, where an electrode array 130 is disposed on both jaw members 110, 120, the electrode arrays 130 cooperate to extend: at least 180 degrees about the cavity 115 defined by jaw members 110, 120; at least 240 degrees; at least 300 degrees; or substantially 360 degrees.

The one or more first electrodes 132 are adapted to connect to a source of electrosurgical energy at a first potential and the one or more second electrodes 134 are adapted to connect to a source of electrosurgical energy at a second, different potential such that, upon energization, electrosurgical energy is conducted from each first leg 133 to the adjacent or nearby second leg(s) 135 (and/or vice versa), and through tissue disposed therebetween to provide bipolar electrosurgical shallow depth ablation of the tissue. More specifically, shallow depth ablation is achieved due to the alternating arrangement of legs 133, 135, about the annular periphery of cavity 115, wherein substantially all of the bipolar electrosurgical energy is conducted from each first leg 133 to the adjacent or nearby second leg(s) 135 (and/or vice versa) and through a shallow depth of tissue therebetween, rather than the electrosurgical energy traversing the cavity 114 between diametrically opposed or nearly opposed legs 133, 135.

In use for ovarian denervation, for example, and with reference to FIGS. 1 and 5A-6, end effector assembly 100 may be manipulated into position such that jaw members 110, 120, in the open position, are disposed with an anatomical structure having a relatively high concentration of ovarian nerves (such as those structures detailed above (see FIG. 1)) extending transversely between jaw members 110, 120. Thereafter, jaw members 110, 120 may be moved to the closed position to capture the tissue structure within cavity 115 such that surfaces 116a, 116b cooperate to surround tissue structure without substantially compressing the tissue structure. In some configurations, by configuring jaw members 110, 120 such that cavity 115 defines a sufficiently large diameter, by maintaining a minimum spacing between jaw members 110, 120 in the closed position (such as, for example, by way of one or more stop members), and/or via compliance or flexion of the jaw members 110, 120, pivot 103, the drive assembly (not shown), and/or other components, a pressure applied to tissue captured within cavity 115 may be, in aspects, less than about 2 kg/cm$^2$, on other aspects, less than about 1 kg/cm$^2$, in still other aspects, less than about 0.5 kg/cm$^2$, although other pressures are also contemplated. By maintaining minimal pressure, thermally ablating tissue is inhibited while shallow depth ablation is facilitated.

With the tissue structure captured within cavity 115, energy may be suppled to one or more first electrodes 132 and one or more second electrodes 134 at different potentials such that, as noted above, shallow depth ablation is achieved due to the alternating arrangement of legs 133, 135, about the annular periphery of cavity 115, wherein substantially all of the bipolar electrosurgical energy is conducted from each first leg 133 to the adjacent or nearby second leg(s) 135 (and/or vice versa). In configurations where multiple first and second electrodes 132, 134, respectively, are provided, energy may be supplied to all electrodes 132, 134 simultaneously such that energy is applied simultaneously to the captured tissue about the annular extent of the electrode array(s) 130, or may be supplied sequentially or in any other suitable pattern such that some portions of the tissue structure captured within cavity 115 receives energy at different times, for different amounts of time, etc. Further, as noted above, depending upon the number and annular extent of the electrode array(s) 130 on one or both of jaw members 110, 120, shallow depth ablation may be provided from about 90 degrees to about 360 degrees about the annular perimeter of the captured tissue structure. The above may be repeated at additional locations along the same or different tissue structures.

Generally referring to FIGS. 1-6, in some configurations, rather than both jaw member 110, 120 including cavities 115a, 115b, only one jaw member 110, 120 may include a cavity 115a, 115b, while the inner surface 114, 124 of the other jaw member 110, 120 extends to overlap with the cavity 115a, 115b to provide a substantially planar surface opposing the cavity 115a, 115b. The cavity 115a, 115b and/or the substantially planar inner surface 114, 124b, in such configurations, may include an electrode array 130 extending at least partially thereabout and/or therealong. The other aspects and features detailed above are equally applicable and useable with these configurations, despite providing a hemicylindrical cavity as compared to cylindrical cavity 215.

Figure 7:
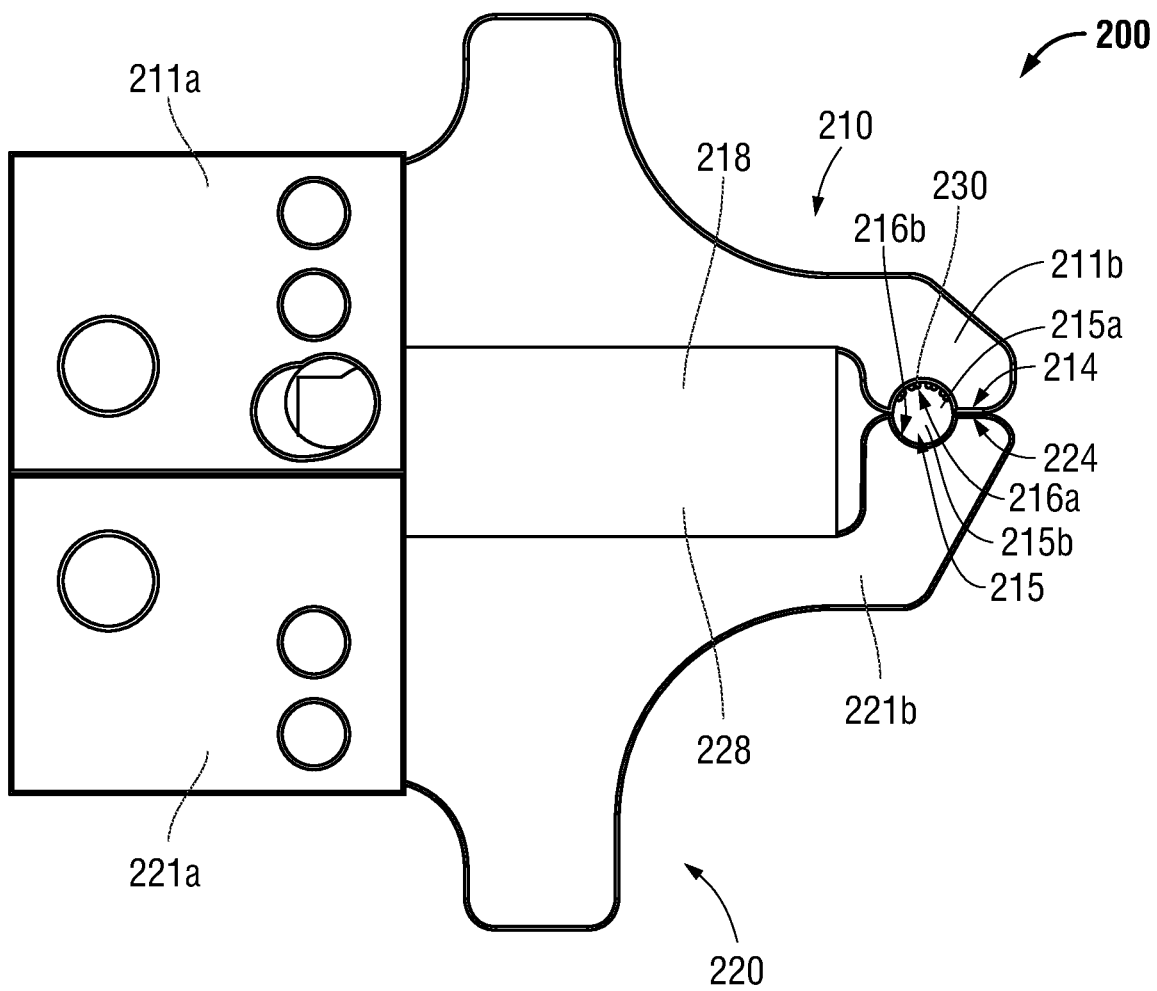
FIG. 7 is a longitudinal, cross-sectional view of another end effector assembly provided in accordance with the present disclosure disposed in a closed position and configured for use with the surgical device of FIG. 2, the surgical device of FIG. 3, the robotic surgical system of FIG. 4, or any other suitable surgical device or system.

Referring to FIG. 7, another end effector assembly provided in accordance with the present disclosure and configured for use with the surgical device of FIG. 2, the surgical device of FIG. 3, the robotic surgical system of FIG. 4, or any other suitable surgical device or system is shown generally identified by reference numeral 200. End effector assembly 200 is similar to and may include any of the features of end effector assembly 100 (FIGS. 5A and 5B), except as explicitly contradicted below. Accordingly, for purposes of brevity, only differences between end effector assembly 200 and end effector assembly 100 (FIGS. 5A and 5B) are described in detail below while similarities are summarily described or omitted entirely.

End effector assembly 200 includes first and second jaw members 210, 220 each including a proximal base end portion 211a, 221a disposed towards the pivot end of end effector assembly 200 and a distal tip end portion 211b, 221b disposed towards the free end of end effector assembly 200. Jaw members 210, 220 are curved along the lengths thereof such that distal tip end portions 211b, 221b are oriented at angles of, in some configurations, from about 45 degrees to about 135 degrees relative to a longitudinal axis defined through proximal base end portions 211a, 221a; in other configurations, from about 60 degrees to about 120 degrees; in still other configurations from about 75 degrees to about 105 degrees; and in still other configurations, about 90 degrees.

Each jaw member 210, 220 further includes a cavity 215a, 215b defined within a respective inner surface 214, 224 thereof towards distal tip end portions 211b, 221b thereof. More specifically, cavities 215a, 215b may be disposed towards distal tip end portions 211b, 221b such that the open end faces of the cylindrical cavity 215 formed by cavities 215a, 215b of jaw members 210, 220 in the closed position are disposed within or at the above-noted angular orientations relative to the longitudinal axis defined through proximal base end portions 211a, 221a. Cavities 215a, 215b are defined by surfaces 216a, 216b, one or both of which includes an electrode array 230.

Each jaw member 210, 220 also includes a recessed portion 218, 228 disposed between proximal base end portions 211a, 221a and cavities 215a, 215b. Recessed portions 218, 228 establish an elongated gap between inner surface 214, 224 in the closed position of jaw members 210, 220, thus enabling end effector assembly 200 to "reach" over interfering tissue structure(s) to reach the target tissue structure and to capture the target tissue structure within cavity 215 while the interfering tissue structure(s) is atraumatically captured within the elongated gap.

Figure 8:
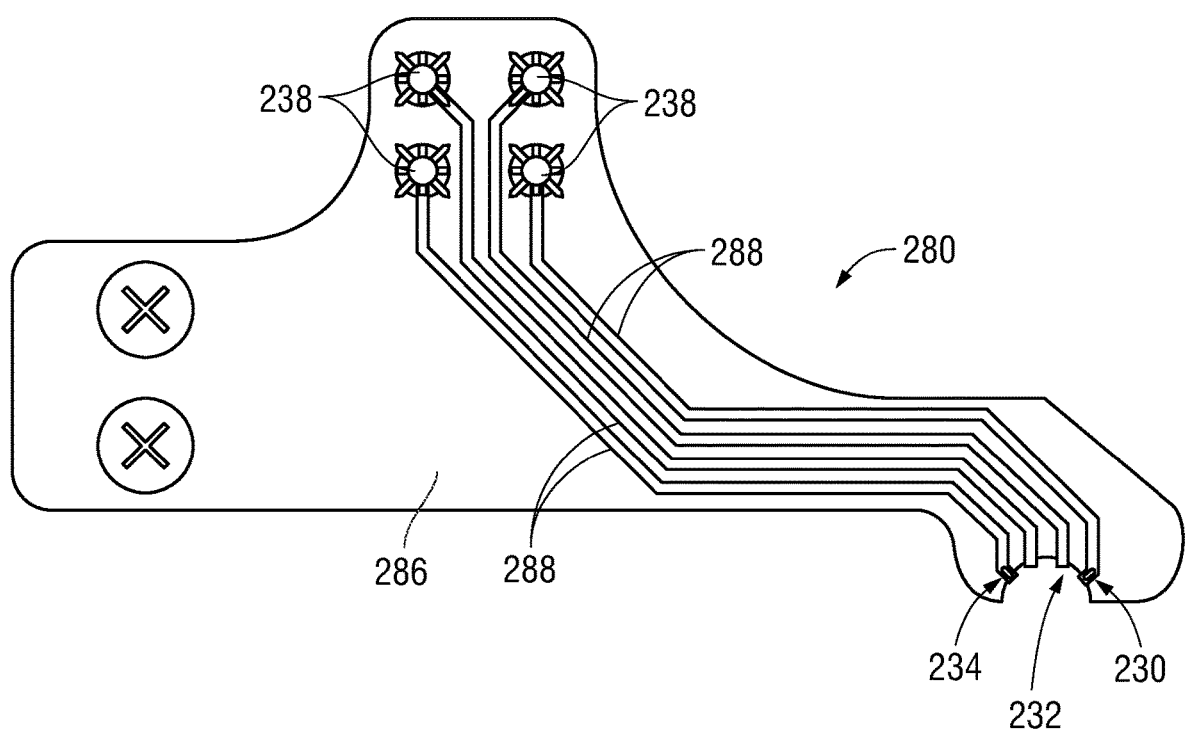
FIG. 8 is a side view of a circuit board of the end effector assembly of FIG. 7.

Turning to FIG. 8, a flex circuit configured for use with end effector assembly 200 (FIG. 7) to define the electrodes thereof and enable the supply of energy thereto is shown generally identified as flex circuit 280. A similar flex circular may be utilized in conjunction with end effector assembly 100 (FIGS. 5A-6). Further, where both jaw members 210, 220 of end effector assembly 200 (FIG. 7) include electrodes, two flex circuits 280 may be provided, one for each jaw member 210, 220 (FIG. 7).

Flex circuit 280 includes a flexible, electrically-insulative substrate 286, e.g., BoPET (biaxially-oriented polyethylene terephthalate), and electrically-conductive circuit traces 288, e.g., copper, printed thereon to define plural electrodes 232, 234 of the one or more electrode arrays 230. Each electrode 232, 234 may include one or more legs (not explicitly shown, see FIG. 6) disposed at distal end portions of the corresponding circuit traces 288. Each electrode 232, 234 further includes a terminal 238 disposed at a proximal end portion of the corresponding circuit trace 288. Terminals 238 enable connection of appropriate electrical leads (not shown) to circuit traces 288 to enable the delivery of electrosurgical energy to electrodes 232, 234. A first common connector (not shown), e.g., clip, may be utilized to connect one electrical lead to the terminals 238 of both first electrodes 232 and a second common connector (not shown), e.g., clip, may be utilized to connect another electrical lead to the terminals 238 of both second electrodes, although separate leads for each of the terminals 238 are also contemplated.

Figure 9:
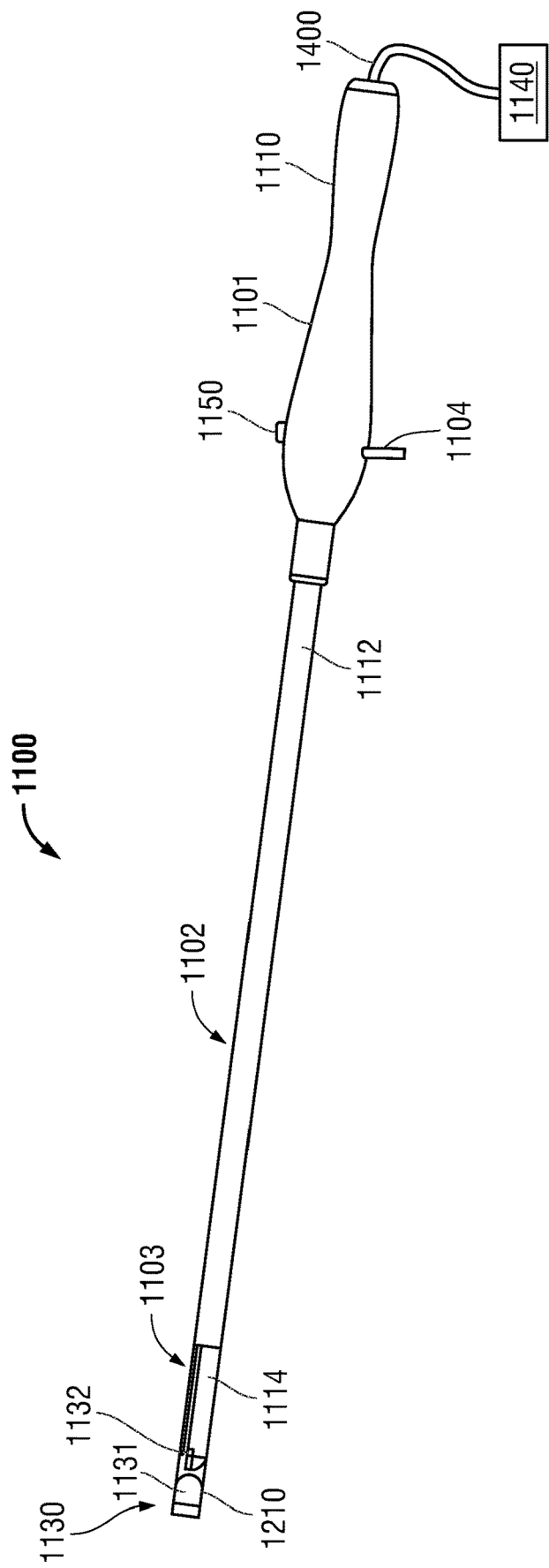
FIG. 9 is a side, perspective view of still another surgical device configured for use in accordance with the present disclosure.

FIGS. 9-11B illustrate another surgical device 1100 in accordance with the present disclosure connected to an electrosurgical generator 1140 (FIG. 9). Surgical device 1100 includes a body 1101, a body handle 1110, and a shaft 1102 extending from the body 1101. Shaft 1102 includes a proximal end portion 1112 coupled to body 1101 and a distal end portion 1114. Shaft 1102 may define a linear configuration, a curved configuration, one or more angled portions, an articulating section or sections, a malleable section or sections, or any other suitable configuration. An actuation rod 1103 extends from body 1101 through shaft 1102. A proximal end portion of actuation rod 1103 is connected to a lever 1104 associated with body 1101 to enable selective actuation, e.g., longitudinal translation, of actuation rod 1103 in response to actuation of lever 1104. As an alternative to including handle 1110 and lever 1104, body 1101 may alternatively be configured to connect to a robotic surgical system, e.g., system 500 (FIG. 4) for robotic control of end effector 1130.

Figure 11A:
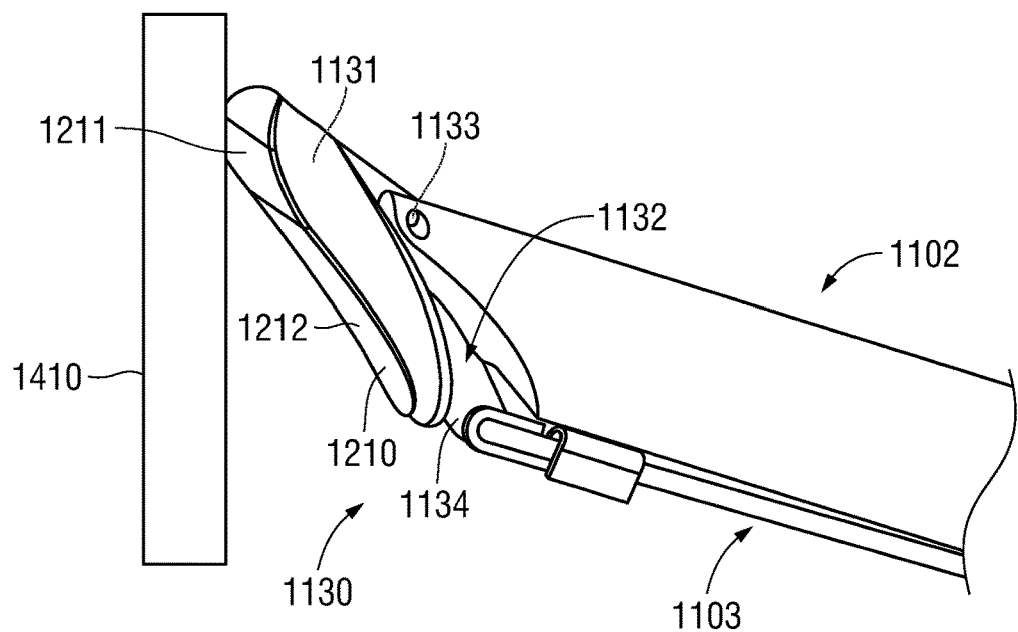
FIGS. 11A and 11B are enlarged, side, perspective views of the end effector of the surgical device of FIG. 9 in use contacting tissue to be treated.
Figure 11B:
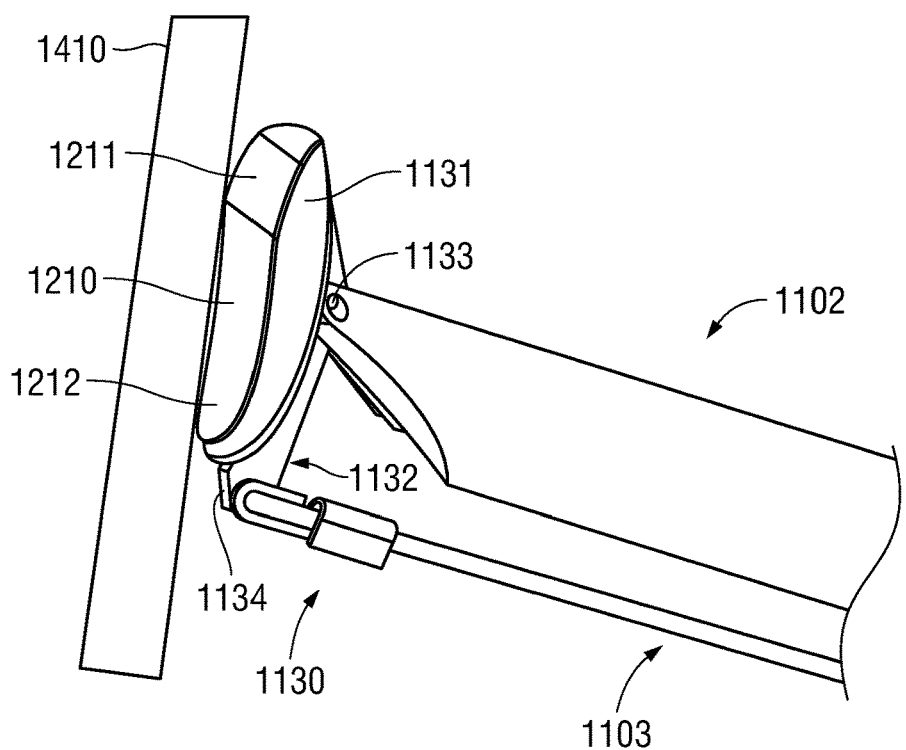

An end effector 1130 is supported at distal end portion 1114 of shaft 1102. End effector 1130 includes a foot 1131 and a pivot assembly 1132. A first portion 1133 of pivot assembly 1132 pivotally couples foot 1131 to distal end portion 1114 of shaft 1102. A second portion 1134 of pivot assembly 1132 is pivotally coupled to a distal portion of actuation rod 1103 at a position offset from first portion 1133 such that translation of actuation rod 1103 moves second portion 1134 of pivot assembly 1132 relative to first portion 1133 of pivot assembly 1132 to thereby pivot foot 1131 relative to distal end portion 1114 of shaft 1102 between a first position (FIG. 11A) and a second position (FIG. 11B).

Figure 10:
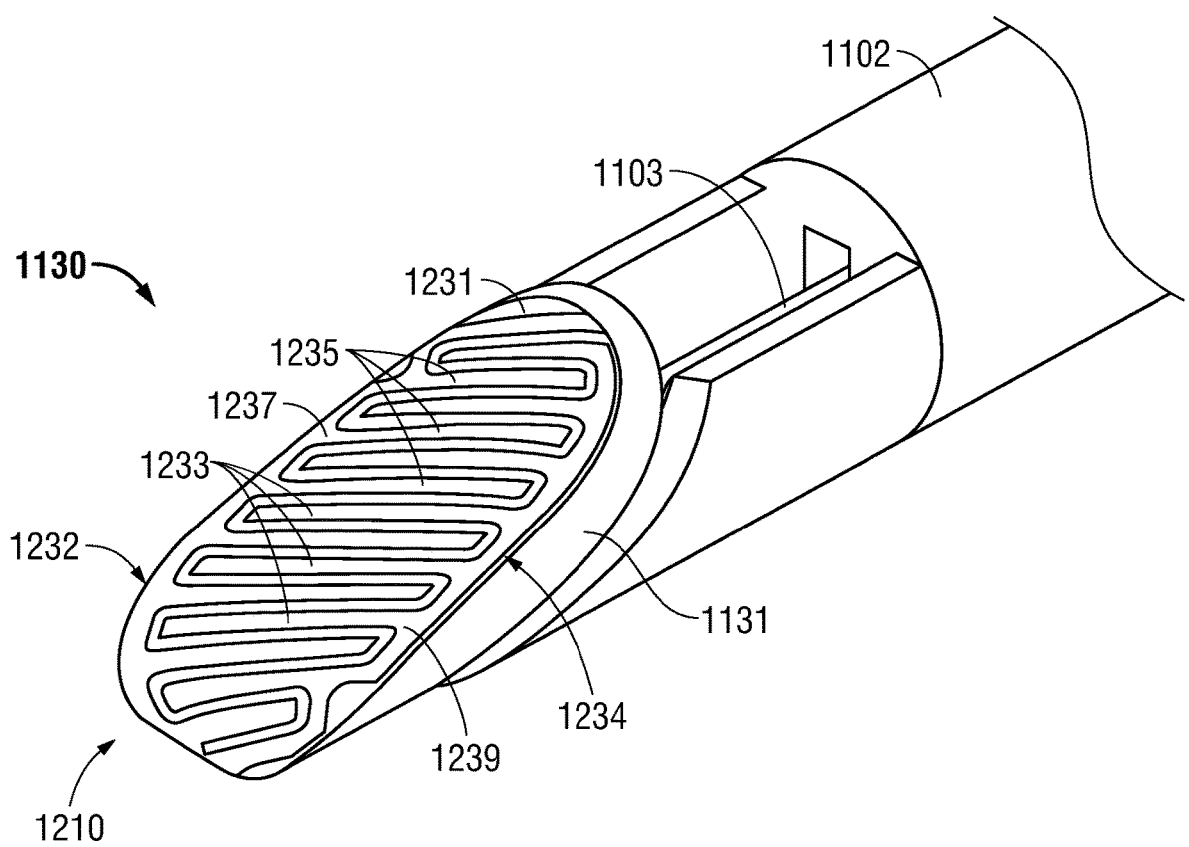
FIG. 10 is an enlarged, bottom, perspective view of an end effector assembly of the surgical device of FIG. 9.

With particular reference to FIG. 10, an electrode array 1210 is disposed on at least a portion of, and in some configurations substantially covers, a distal face of foot 1131. Electrode array 1210 may be configured similar to any of the electrode array configurations detailed above or in any other suitable manner. More specifically, electrode array 1210 may be a flex circuit including an insulative substrate 1231 adhered or otherwise attached to distal face of foot 1131 and having printed thereon traces to form one or more first electrodes 1232 and one or more second electrodes 1234. First and second electrodes 1232, 1234 are electrically isolated from one another and configured to be energized to different potentials. Each electrode 1232, 1234 includes a plurality of electrode legs 1233, 1235 and may further include a common connector 1237, 1239 connecting each of the respective legs 1233, 1235 thereof. Electrodes 1232, 1234 are arranged such that electrode legs 1233, 1235 are arranged in alternating, spaced-apart relation extending over at least a portion of the distal face of foot 1131. In some configurations, such as illustrated in FIG. 10, the common connector 1237, 1239 of each electrode 1232, 1234 extends along an opposing side and/or end of the distal face of foot 1131 and the corresponding legs 1233, 1235 extend therefrom across the distal face of foot 1131 such that the legs 1233, 1234 extend from opposing sides and/or ends of the distal face of foot 1131 in spaced-apart, alternating fashion relative to one another.

Referring again to FIGS. 9-11B, electrode array 1210 is connected to electrosurgical generator 1140 via cable 1400 to enable the supply of bipolar electrosurgical energy to electrode array 1210 for application to tissue in contact with the distal face of foot 1131 for shallow depth ablation thereof. Similarly as detailed above, the configuration of electrode array 1210 facilitates shallow depth ablation due to the conduction of electrosurgical energy from each first leg 1233 to the adjacent or nearby second leg(s) 1235 (and/or vice versa), and through tissue disposed therebetween.

The distal face of foot 1131 includes a toe portion 1211 and a heel portion 1212. Heel portion 1212 is positioned proximal of toe portion 1211 when actuation rod 1103 is disposed in the first position (FIG. 11A) such that tissue treatment is provided to a relatively smaller tissue treatment area at toe portion 1211 when toe portion 1211 contacts tissue 1410. On the other hand, heel portion 1212 substantially aligns with toe portion 1211 when actuation rod 1103 is disposed in the second position (FIG. 11B) such that a relatively larger tissue treatment area covering substantially all of the distal face of foot 1131 is provided to treat tissue in contact with the distal face of foot 1131. The distal face of foot 1131 may be contoured to facilitate tissue treatment with the relatively smaller and/or relatively larger treatment areas of the distal face of foot 1131. Further, electrode array 1210 (FIG. 10) may be configured to enable selective activation of different portions thereof such as, for example, to enable activation of only the electrode legs 1233, 1235 (FIG. 10) of the toe portion 1211 in the first position (FIG. 11A) and to enable activation of all electrode legs 1233, 1235 (FIG. 10) in the second position (FIG. 11B).

With respect to use of surgical device 1100 for ovarian denervation, for example, foot 1131 of end effector 1130 may be manipulated into position and actuation rod 1103 actuated such that at least a portion of the distal face of foot 1131 contacts an anatomical structure having a relatively high concentration of ovarian nerves (such as those structures detailed above (see FIG. 1)). More specifically, foot 1131 may be pivoted such that the relatively smaller treatment area or the relatively larger treatment area contacts the anatomical structure, depending upon the tissue(s) to be treated and/or other factors.

Once foot 1131 of end effector 1130 is positioned in contact with tissue to be treated as noted above, energy may be supplied to electrode array 1210 such that shallow depth ablation is achieved. End effector 1130 may be moved along the tissue structure and/or pivoted to treat different anatomical structures.

Figure 12:
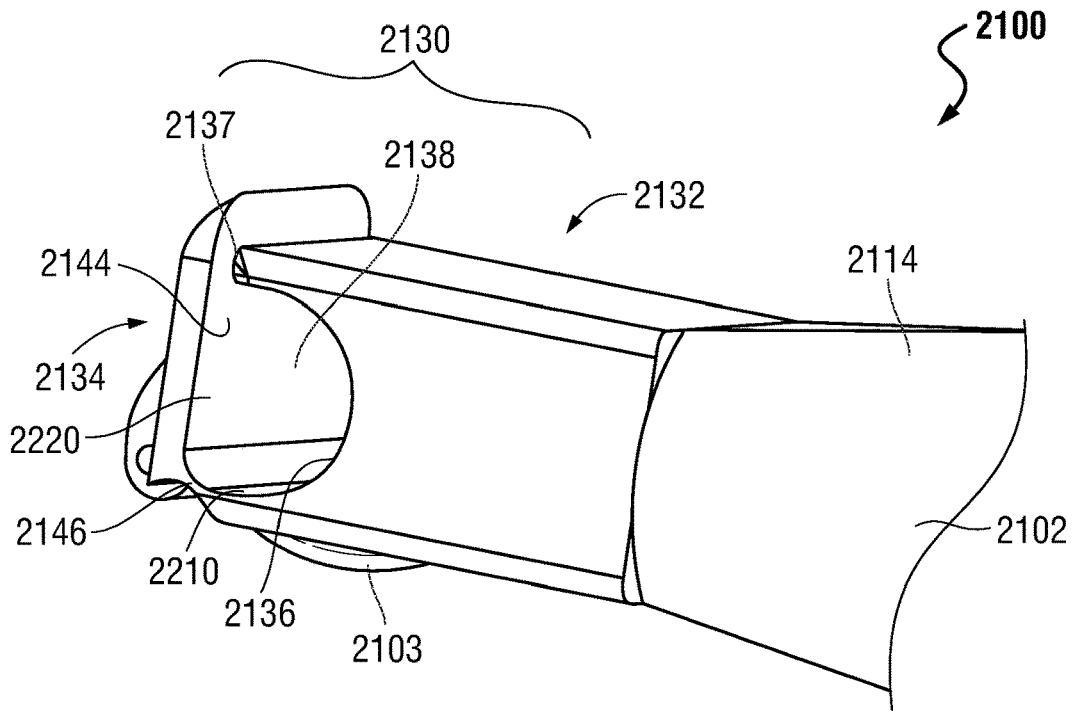
FIG. 12 is a side, perspective view of a distal portion of yet another surgical device configured for use in accordance with the present disclosure.
Figure 13:
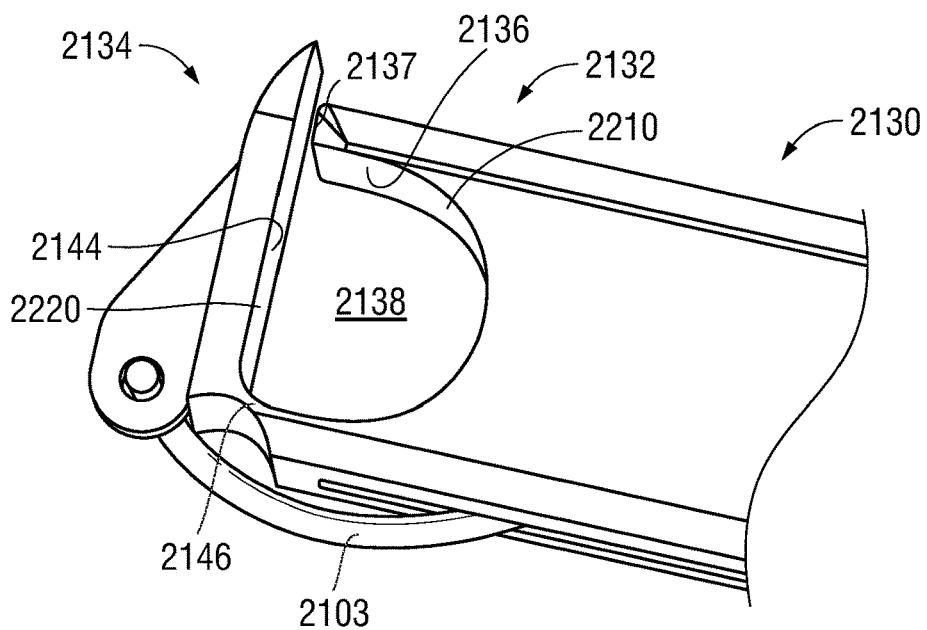
FIG. 13 is an enlarged, side, perspective view of an end effector assembly of the surgical device of FIG. 12.
Figure 14:
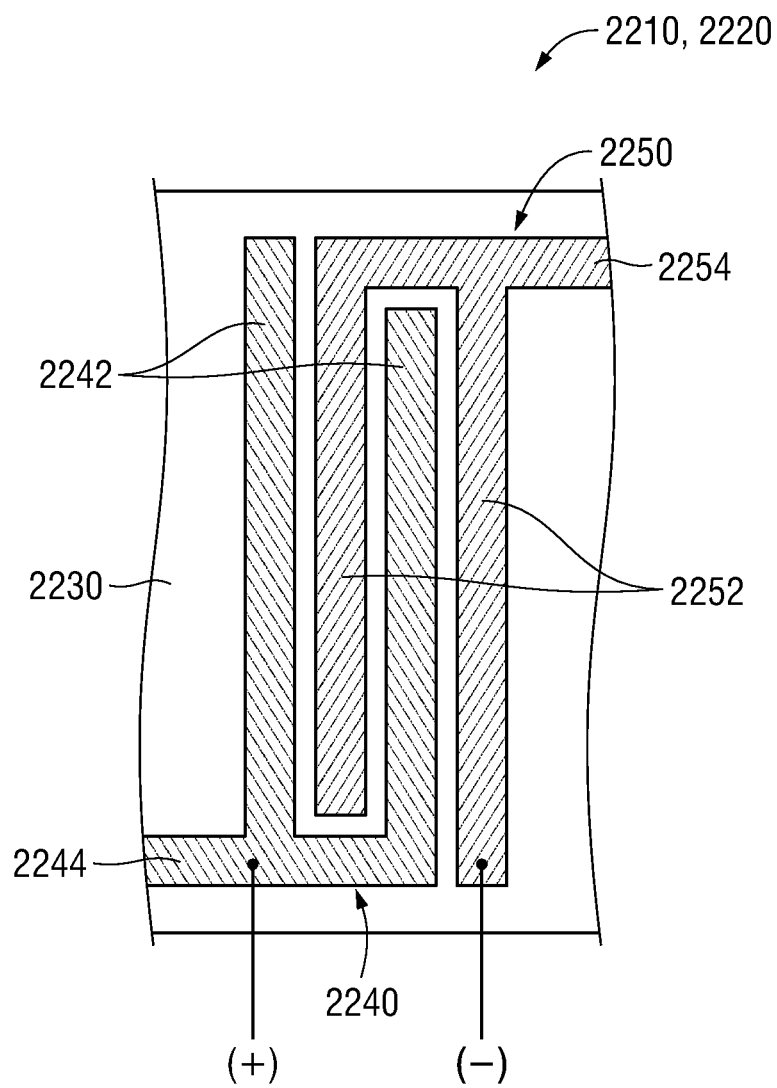
FIG. 14 is a schematic illustration illustrating an electrode configuration at a contact area between first and second jaw members of the end effector assembly of the surgical device of FIG. 12.

Referring to FIGS. 12-14, another surgical device 2100 in accordance with the present disclosure is configured to connect to an electrosurgical generator, e.g., generator 90 (FIG. 3) or 1140 (FIG. 9). Surgical device 2100 may be similar to surgical device 1100 (FIG. 9) and, thus, only differences therebetween are described in detail below while similarities are summarily described or omitted entirely.

Surgical device 2100 includes a body (not shown) including a handle and a lever or other suitable actuator. Surgical device 2100 further includes a shaft 2102 extending distally from the body. An actuation rod 2103 extends from the body through and/or along shaft 2102. A proximal end portion of actuation rod 2103 is connected to the lever to enable selective actuation, e.g., longitudinal translation, of actuation rod 2103 in response to actuation of the lever. Alternatively, the body of surgical device 2100 may be configured to connect to a robotic surgical system, e.g., system 500 (FIG. 4), for robotic control of actuation rod 2103.

An end effector 2130 is supported at a distal end portion 2114 of shaft 2102. End effector 2130 includes a first, fixed jaw member 2132 and a second, movable jaw member 2134. One of the jaw members, e.g., first jaw member 2132, defines an includes a tissue-contacting surface 2136 defining a cavity 2138 therein. A substantially planar portion 2137 of tissue-contacting surface 2136 may be disposed on the free-end side of cavity 2138. Cavity 2138 defines a substantially hemicylindrical configuration, extends transversely across jaw member 2132, and is open at either end thereof. The open side of cavity 2138 may be oriented distally or in any other suitable orientation. Further, although cavity 2138 is shown having a hemicylindrical configuration, other substantially hemicylindrical configurations are also contemplated such as, for example, hemi-oval-shaped configurations, higher-order polygonal configurations that generally approximate a hemicylinder, e.g., a hemi-octagon, hemi-decagon, hemi-dodecagon, etc., and other suitable hemicylindrical-approximating configurations.

The other jaw member, e.g., second jaw member 2134, defines a substantially planar tissue-contacting surface 2144. Tissue contacting surfaces 2136, 2144 are configured to oppose one another in a closed position of jaw members 2132, 2134 to capture tissue therebetween and/or at least partially within cavity 2138. More specifically, second jaw member 2134 is movably coupled to first jaw member 2132, e.g., via a living hinge 2146 or other suitable movable structure such as, for example, a pivot pin, linkages, etc., to enable movement of second jaw member 2134 relative to first jaw member 2132 between spaced-apart and approximated positions. In the spaced-apart position, jaw member 2134 may be disposed at an angle relative to jaw member 2132 of, in configurations, at least 45 degrees, at least 60 degrees, at least 75 degrees, or about 90 degrees. Tissue-contacting surface 2136 of first jaw member 2132 may be oriented substantially perpendicularly relative to a longitudinal axis of shaft 2102 and, thus, in the approximated position of jaw member 2134, tissue-contacting surface 2144 of second jaw member 2134 may likewise be oriented substantially perpendicularly relative to a longitudinal axis of shaft 2102 and parallel to the planar portions of tissue-contacting surface 2136, although other configurations are also contemplated.

Actuation rod 2103 is pivotably coupled to second jaw member 2134 at a position offset from living hinge 2146 such that, in response to translation of actuation rod 2103, second jaw member 2134 is moved between the spaced-apart and approximated positions (depending upon the direction of translation of actuation rod 2103).

Continuing with reference to FIGS. 12-14, electrode array portions 2210, 2220 are disposed on at least a portion of, and in some configurations to substantially cover, either or both of tissue contacting surfaces 2136, 2144. With respect to tissue-contacting surface 2136, electrode array portion 2210 may be disposed on at least a portion of substantially planar portion 2137 of tissue-contacting surface 2136 and/or on the portion of tissue-contacting surface 2136 that defines cavity 2138. Electrode array portions 2210, 2220 may be configured similar to any of the electrode array configurations detailed above or in any other suitable manner. In some configurations, electrode array portions 2210, 2220 are formed together on a single substrate that extends from tissue-contacting surface 2136, along an interior surface of living hinge 2146, to tissue-contacting surface 2144.

Electrode array portions 2210, 2220 may be flex circuits, part of a single, continuous flex circuit, or interconnected by a flex circuit. Electrode array portions 2210, 2220 include insulative substrate portions 2230 adhered or otherwise attached to tissue contacting surfaces 2136, 2146 and/or living hinge 2146 and having printed thereon traces to form one or more first electrodes 2240 and one or more second electrodes 2250. Electrode array portions 2210, 2220 may be configured similar to electrode array 1210 (FIG. 10), any other electrode array detailed herein, combinations thereof, or in any other suitable manner. In particular, in some configurations, first and second electrodes 2240, 2250 of electrode array portions 2210, 2220 each include a plurality of electrode legs 2242, 2252 and may further include a common connector 2244, 2254 connecting each of the respective legs 2242, 2252 thereof. Thus, electrodes 2240, 2250 are arranged in alternating, spaced-apart relation to form an intertwined configuration and extend over at least a portion of tissue contacting surface 2136 and/or tissue contacting surface 2144. The electrode arrangement within cavity 2138 may define any suitable configuration such as those detailed hereinabove.

In the approximated position of jaw members 2132, 2134, substantially planar portion 2137 of tissue-contacting surface 2136 and a portion of tissue-contacting surface 2144 towards a free end portion of jaw member 2134 may contact one another. However, electrode array portions 2210, 2220 are oriented on jaw members 2132, 2134 and relative to one another such that, when such contact occurs, the plurality of electrode legs 2242, 2252 only contact electrode legs 2242, 2252 of similar polarity and/or contact insulative substrate portions 2230 of the opposing tissue-contacting surface 2136, 2144. In this manner, shorting is inhibited and appropriate electrode spacing is maintained.

With respect to use of surgical device 2100, e.g., for ovarian denervation, end effector assembly 2130 may be manipulated into position with jaw member 2134 disposed in the spaced-apart position. Jaw member 2134, in the spaced-apart position, may be used to manipulate tissue and/or to facilitate scooping tissue, e.g., the neurovascular ligament, into cavity 2138 of jaw member 2130. The free end of jaw member 2134, in the spaced-apart position, may also be utilized to facilitate insertion into and/or access to a surgical site. Once the appropriate tissue is received within cavity 2138 of jaw member 2132, or positioned to enable urging thereof into cavity 2138, jaw member 2134 may be pivoted to the approximated position. In the approximated position, tissue is captured within the now closed hemicylindrical cavity 2138 defined by cooperating jaw members 2132, 2134. In this position, substantially complete contact between the captured tissue and tissue contacting surfaces 2136, 2144 while maintaining minimal pressure applied to the captured tissue is achieved to facilitate shallow depth ablation or other suitable treatment. Energy may be supplied to electrode array portions 2210, 2220 to achieve shallow depth ablation of the captured tissue. End effector 2130 may be moved along the tissue structure or repositioned to treat different anatomical structures.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical device for shallow depth ablation, the surgical device comprising:
an end effector assembly, including:
first and second jaw members, at least one of the first or second jaw members movable relative to the other between an open position and a closed position, each of the first and second jaw members including an inner surface oriented towards the inner surface of the other of the first and second jaw members, an outer surface, and a hemicylindrical surface recessed relative to the inner surface to define a hemicylindrical cavity, wherein, in the closed position of the first and second jaw members, the hemicylindrical surfaces cooperate to define a cylindrical cavity, the cylindrical cavity extending transversely across the first and second jaw members and open at either end of the cylindrical cavity, wherein, in the closed position of the first and second jaw members, the first and second jaw members are configured to capture tissue within the cylindrical cavity, wherein the inner surfaces of the first and second jaw members are exposed continuously over areas defined laterally from first lateral sides of the respective first and second jaw members to second, opposite lateral sides of the respective first and second jaw members and longitudinally from proximal end portions of the respective first and second jaw members to the hemicylindrical surfaces of the respective first and second jaw members; and
at least one electrode array confined to within the hemicylindrical cavity of at least one of the first or second jaw members and including a plurality of first electrode portions and a plurality of second electrode portions, the first and second electrode portions disposed on or within at least one of the hemicylindrical surfaces and extending annularly at least partially about the at least one hemicylindrical surface, the inner surfaces of the first and second jaw members one of electrically insulative or electrically isolated from the at least one electrode array,
wherein, the plurality of first electrode portions is configured to be energized with electrosurgical energy at a potential, and the plurality of second electrode portions is configured to be energized with electrosurgical energy at a different potential to thereby conduct electrosurgical energy within the hemicylindrical cavity of at least one of the first or second jaw members and between adjacent electrode portions of different potential and through captured tissue to affect shallow depth ablation of captured tissue in the closed position of the first and second jaw members.

2. The surgical device according to claim 1, wherein the plurality of first electrode portions and the plurality of second electrode portions are arranged in alternating, spaced-apart relation annularly about at least a portion of the at least one hemicylindrical surface.

3. The surgical device according to claim 2, wherein each electrode portion of the plurality of first electrode portions is a first electrode leg extending in substantially parallel orientation relative to a longitudinal axis of the hemicylindrical cavity defined by the at least one hemicylindrical surface and wherein each electrode portion of the plurality of second electrode portions is a second electrode leg extending in substantially parallel orientation relative to a longitudinal axis of the hemicylindrical cavity defined by the at least one hemicylindrical surface.

4. The surgical device according to claim 1, wherein the first and second electrode portions extend annularly at least 90 degrees about the at least one hemicylindrical surface.

5. The surgical device according to claim 1, wherein the first and second electrode portions extend annularly at least 180 degrees about the at least one hemicylindrical surface.

6. The surgical device according to claim 1, wherein the at least one electrode array includes a flex circuit.

7. The surgical device according to claim 1, wherein the at least one electrode array includes a flexible, insulative substrate and wherein the first and second electrode portions are printed onto the substrate as conductive traces.

8. The surgical device according to claim 1, wherein the first and second jaw members are substantially linear.

9. The surgical device according to claim 1, wherein the first and second jaw members are curved along at least a portion of lengths thereof.

10. The surgical device according to claim 1, wherein at least one of the first or second jaw members is at least partially compressible to reduce an amount of pressure applied to tissue captured within the cylindrical cavity.

11. The surgical device according to claim 1, wherein the inner surfaces of the first and second jaw members are substantially planar.

12. The surgical device according to claim 1, wherein the inner surfaces of the first and second jaw members are electrically conductive and electrically isolated from the at least one electrode array.

13. The surgical device according to claim 1, wherein the inner surfaces of the first and second jaw members are electrically insulative.

14. The surgical device according to claim 13, wherein electrically insulated bodies of the first and second jaw members define the electrically insulative inner surfaces of the first and second jaw members.

15. The surgical device according to claim 13, wherein electrically insulative coatings disposed on bodies of the first and second jaw members define the electrically insulative inner surfaces of the first and second jaw members.

* * * * *